United States Patent
O'Lenick et al.

(10) Patent No.: US 7,858,075 B2
(45) Date of Patent: Dec. 28, 2010

(54) SPIDER ESTERS IN PERSONAL CARE APPLICATIONS

(75) Inventors: Kevin A. O'Lenick, Dacula, GA (US); Anthony J. O'Lenick, Jr., Dacula, GA (US)

(73) Assignee: SurfaTech Corporation, Dacula, GA (US)

(*) Notice: Subject to any disclaimer, the term of this patent is extended or adjusted under 35 U.S.C. 154(b) by 150 days.

(21) Appl. No.: 12/380,305

(22) Filed: Feb. 27, 2009

(65) Prior Publication Data

US 2009/0170943 A1    Jul. 2, 2009

Related U.S. Application Data

(62) Division of application No. 11/124,018, filed on May 9, 2005, now Pat. No. 7,473,707.

(51) Int. Cl.
*A61K 8/72*    (2006.01)
(52) U.S. Cl. .................................................. 424/70.11
(58) Field of Classification Search ........................ None
See application file for complete search history.

(56) References Cited

U.S. PATENT DOCUMENTS 6,362,353 B1    3/2002    Ellis et al.
7,473,707 B1    1/2009    O'Lenick

FOREIGN PATENT DOCUMENTS

JP    55160710 A  *  12/1980

OTHER PUBLICATIONS

Translation of JP 55160710 by USPTO.*

* cited by examiner

*Primary Examiner*—Robert A Wax
*Assistant Examiner*—Bethany Barham

(57) ABSTRACT

The present invention is drawn to a process for providing emolliency to the skin using a series so called "spider esters". These esters are derived from poly-hydroxy functional compounds sequentially reacted with ethylene oxide or propylene oxide, followed by the reaction of the alkoxylate with fatty acid. The resulting products are called spider esters because they resemble the spider, wherein appendages are alkoxylated esters. The restrictions this orientation imposes on rotation allows for the preparation of polar esters that have little or no water solubility, and provide both moisturization to the skin and emolliency by reducing transepidermal water loss.

10 Claims, No Drawings

SPIDER ESTERS IN PERSONAL CARE APPLICATIONS

RELATED APPLICATION

This application is a divisional application of which is in turn a divisional application of Ser. No. 11/124,018 filed May 9, 2005, now U.S. Pat. No. 7,473,707.

FEDERAL SPONSORSHIP

There is no federal sponsorship on the present invention.

FIELD OF THE INVENTION

The present invention is drawn to a process for providing emolliency to the skin using a series so called "spider esters". These esters are derived from poly-hydroxy functional compounds sequentially reacted with ethylene oxide or propylene oxide, followed by the reaction of the alkoxylate with fatty acid. The resulting products are called spider esters because they resemble the spider, wherein appendages are alkoxylated esters. The restrictions this orientation imposes on rotation allows for the preparation of polar esters that have little or no water solubility, and provide both moisturization to the skin and emolliency by reducing transepidermal water loss.

BACKGROUND OF THE INVENTION

The use of alkoxyated non-ionic as surface active agents is well known. The ethoxylation of fatty alcohols results in compounds that have both water soluble and oil soluble groups. The result is a so called "surfactant", a contraction for surface active agent. The addition of ethylene oxide to fatty alcohol results in increasing water solubility.

The term "HLB" was first employed by the lab staff of the Atlas Powder Co. in America. This means the balance between the oil soluble and water soluble moieties in a surface active molecule, and is expressed as the "Hydrophile-Liphophile Balance". A more oil-soluble emulsifier shows a lower HLB and a more water-soluble emulsifier shows the reverse. HLB is a very useful method in selecting an emulsifier, but it still has several limitations to application for every surfactant.

The HLB system developed by Griffin some 50 years ago. The system depends upon the observation that the solubility of the surfactant is related to the percentage by weight of polyoxyalkylene portion of the molecule and is relatively independent of the nature of the fatty group.

HLB Value=% EO/5

| Water Dispersibility | HLB | % EO. |
| --- | --- | --- |
| Not dispersible | 1-4 | up to 20% |
| Poorly dispersible | 4-6 | 20%-30% |
| Milky dispersion | 6-8 | 30%-40% |
| Stable milky dispersion | 8-10 | 40%-50% |
| Translucent to clear | 10-13 | 50%-65% |
| Clear Solution | 13+ | Over 65% |

| HLB | Application. |
| --- | --- |
| 4-6 | W/O Emulsifier |
| 7-9 | Wetting Agent |
| 8-18 | O/W Emulsifier |
| 13-15 | Detergents |
| 15-18 | Solubilizers |

The HLB system has some very distinct situations I which the applicability breaks down. It is designed for ethoxylated products, specifically linear alcohol ethoxylates. It is not useful when applied to Guerbet alcohol ethoxylates due to the branching. We have also surprisingly and unrepentantly found that certain esters that are linked together through a linking group are not surfactants, despite high levels of ethoxylates. We have dubbed these spider esters since the structure is reminiscent of a spider. The crosslinking group is the body of the spider and the ethoxylated fatty esters are the legs. A specific order is also needed. The ethoxylated needs to be closest to the body of the spider and the fatty group at the foot end. While not wanting to be limited by any one theory we believe this orientation limits rotation of the polyoxyalkylene group and causes the molecule to be incapable of orientation at the surface of a water oil interface. Such orientation results in water solubility caused by the polyoxyalkylene groups going into the water and the oil soluble group going into the oil phase. The result is an ester that contains an appreciable amount of polar polyoxyalkylene group but is water insoluble. This is a very interesting material in that it represents a polar rich oil in which polar and ionic materials may be dissolved and applied in an oil phase. This is a critical concept for delivery of antioxidants, free radical scavengers, sun screens and the like to the skin.

Surfactants are by definition compounds that remove natural oils from the skin. The removal of oil from the skin is a stripping process that damages the skin and provides dry chapped skin. Surfactants in the process of emulsification, detergency or wetting have a cleansing effect in removing soil form the skin, but concurrently cause dry skin. This process results in dry skin and cosmetically unacceptable appearance to the skin. Dry skin is a major consumer problem in the cosmetic industry.

It is generally accepted that there are two different mechanisms of providing emolliency to the skin. The first is to provide moisture in so called moisturizing compounds. These compounds allow moisture to penetrate the skin. The alternate method is to trap moisture inside the skin providing a barrier that does not allow moisture to be lost. The barrier is a water insoluble oil that when placed on the skin keeps moisture from evaporating. It is clear that the two different mechanisms are mutually exclusive. That is, if an emollient oil is applied to the skin, not only can moisture not exit the skin, but moisture cannot enter, traversing the barrier. If a moisturizer is applied to the skin it must be applied to a barrier free skin. Simply put you cannot have effective moisturization on skin with a barrier present, since it will not penetrate. There is a long felt need for a technology that provides moisturization and emolliency. This requires a non-surface active polar oil that can simultaneously have water binding sites and oil soluble sites. Such a combination of properties has been elusive until the process of the current invention was discovered.

We have unexpectantly and surprisingly found that molecules of the present invention, by virtue of having the polyoxyalkylene group bonded on one side to a fatty group and on the other to a common backbone, compounds that have polyoxyalkylene contents that would render them water soluble if the they were present in non-spider esters. These polar esters link a fatty group through a polyoxyalkylene group to a common polymeric backbone. While not wanting to be held to one specific theory, the functionality of the present molecules has to do with the balance between the fatty group and the water soluble group and requires limitation on the orientation of the resulting polymer. The result is an ester that has little or no water solubility, an ability to deliver water and no surface activity.

By polyoxyalkylene groups is meant polyoxyethylene groups $-(-(CH_2CH_2O)_aH)$, polyoxypropylene groups $(-CH_2CH(CH_3)O)_bH)$ or mixtures thereof $(-(CH_2CH_2O)a-CH_2CH(CH_3)O)_bH)$.

THE INVENTION

Object of the Invention

One objective of the present invention is to provide a series of unique spider esters that are water insoluble yet contain large polar groups. These polar groups solubilize ionic and polar materials providing delivery of polar materials that would otherwise be oil insoluble from a polar oil phase.

Another objective of the present invention is to provide a vehicle to improve oil solubility of antioxidants, sunscreens and free radical scavenger to allow for through and efficient delivery of these materials to the skin in a polar oil phase.

Other objects of the invention will become clear as one reads the following specifications and disclosures.

SUMMARY OF THE INVENTION

The present invention relates to a process for providing moisturization and emolliency to the skin in a simultaneous process. The process comprises contacting the skin with an effective moisturization concentration of a so called "spider ester".

These so-called spider ester of the present invention have a fatty group connected through a short polyoxyalkylene group to a common linkage group. The so-called linkage group is a consequence of the choice of the proper poly-hydroxy compound. The resulting ester looks like a spider, having a body (linkage group) and multi legs, having a low number of polyoxyalkylene groups present (the leg) and fatty ester groups (the spider's feet). This type of molecule allows groups that are oil soluble (fatty ester "feet"), water attracting (polyoxyalkylene groups (the spider's legs) and a linkage group (poly hydroxy raw material group). The compounds when applied to the skin allow for moisturization, by delivery of moisture from the spider's leg (polyoxyalkylene group), protection from evaporation of moisture (the spider's "fatty feet"), and no surface active properties, due to the lack of rotation caused by the linkage group, resulting in a very efficient multi-dimensional moisturizing agent. The process of using this compound in moisturization of the skin comprises contacting the skin with an effective moisturizing concentration of the spider esters of the present invention.

DETAILED DESCRIPTION OF THE INVENTION

The present invention is directed to a process for moisturizing the skin which comprises contacting the skin with an effective moisturizing concentration of a compound selected from the group consisting of:

(a) glycerin spider esters conforming to the following structure;

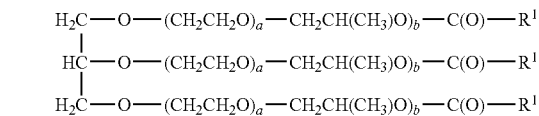

wherein;
a is an integer ranging from 0 to 4;
b is an integer ranging from 0 to 4, with the proviso that a+b ranges from 1 to 4;
$R^1$ is alkyl having 7 to 21 carbon atoms;

(b) glycol spider esters conform to the following structure;

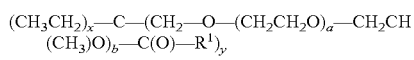

wherein;
a is an integer ranging from 0 to 4;
b is an integer ranging from 0 to 4, with the proviso that a+b ranges from 1 to 5;
$R^1$ is alkyl having 7 to 21 carbon atoms;
y is 4 or 3;
x equals 4−y;
$R^1$ is alkyl having 7 to 21 carbon atoms;

and (c) sorbitol spider esters conforming to the following structure;

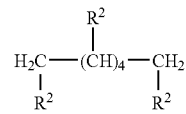

wherein;
$R^2$ is $-(CH_2CH_2O)_a-CH_2CH(CH_3)O)_b-C(O)-R^1$
a is an integer ranging from 0 to 4;
b is an integer ranging from 0 to 4, with the proviso that a+b ranges from 1 to 5;
$R^1$ is alkyl having 7 to 21 carbon atoms;
y is an integer 1, 2, 3, or 4;
x equals y−4.

Preferred Embodiment

In a preferred embodiment the process is conducted using a glyceryl spider ester.

In a preferred embodiment the glyceryl spider ester b is 0.
In a preferred embodiment the glyceryl spider ester a is 0.
In a preferred embodiment the glyceryl spider ester a is not 0 and b is not 0.
In a preferred embodiment the glyceryl spider ester a is 1, b is 1.
In a preferred embodiment the glyceryl spider ester $R^1$ is alkyl having 7 carbon atoms.
In a preferred embodiment the glyceryl spider ester $R^1$ is alkyl having 9 carbon atoms.
In a preferred embodiment the glyceryl spider ester $R^1$ is alkyl having 11 carbon atoms.
In a preferred embodiment the glyceryl spider ester $R^1$ is alkyl having 13 carbon atoms.

In a preferred embodiment the glyceryl spider ester $R^1$ is alkyl having 19 carbon atoms.

In a preferred embodiment the glyceryl spider ester $R^1$ is alkyl having 21 carbon atoms.

In another preferred embodiment the process is conducted using a glycol spider ester.

In a preferred embodiment the glycol spider ester y is 4.

In a preferred embodiment the glycol spider ester y is 3.

In a preferred embodiment the glycol spider ester y is 4, a is 0 and b is 2.

In a preferred embodiment the glycol spider ester y is 3, a is 0 and b is 2.

In a preferred embodiment the glycol spider ester b is 0.

In a preferred embodiment the glycol spider ester a is 0.

In a preferred embodiment the glycol spider ester a is not 0 and b is not 0.

In a preferred embodiment the glycol spider ester a is 1, b is 1.

In a preferred embodiment the glycol spider ester $R^1$ is alkyl having 7 carbon atoms.

In a preferred embodiment the glycol spider ester $R^1$ is alkyl having 9 carbon atoms.

In a preferred embodiment the glycol spider ester $R^1$ is alkyl having 11 carbon atoms.

In a preferred embodiment the glycol spider ester $R^1$ is alkyl having 13 carbon atoms.

In a preferred embodiment the glycol spider ester $R^1$ is alkyl having 19 carbon atoms.

In a preferred embodiment the glycol spider ester $R^1$ is alkyl having 21 carbon atoms.

In a preferred embodiment the process is conducted using a sorbitol spider ester.

In a preferred embodiment the sorbitol spider ester b is 0.

In a preferred embodiment the sorbitol spider ester a is 0.

In a preferred embodiment the sorbitol spider ester a is not 0 and b is not 0.

In a preferred embodiment the sorbitol spider ester a is 1, b is 1.

In a preferred embodiment the sorbitol spider ester $R^1$ is alkyl having 7 carbon atoms.

In a preferred embodiment the sorbitol spider ester $R^1$ is alkyl having 9 carbon atoms.

In a preferred embodiment the sorbitol spider ester $R^1$ is alkyl having 11 carbon atoms.

In a preferred embodiment the sorbitol spider ester $R^1$ is alkyl having 13 carbon atoms.

In a preferred embodiment the sorbitol spider ester $R^1$ is alkyl having 19 carbon atoms.

In a preferred embodiment the sorbitol spider ester $R^1$ is alkyl having 21 carbon atoms.

EXAMPLES

Glyceryl Alkoxylates

Glyceryl Alkoxylates were prepared by Siltech LLC, of Dacula, Ga. They are made by addition of ethylene oxide, propylene oxide or mixtures thereof to glycerin. They conform to the following structure;

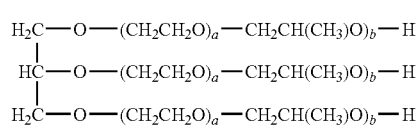

wherein;

a is an integer ranging from 0 to 4;

b is an integer ranging from 0 to 4, with the proviso that a+b ranges from 1 to 4.

Raw Material Examples

| Example | a | b |
|---------|---|---|
| 1 | 0 | 1 |
| 2 | 1 | 1 |
| 3 | 2 | 2 |
| 4 | 1 | 0 |
| 5 | 3 | 1 |
| 6 | 1 | 3 |

Glycol Alkoxylates

Glycol Alkoxylates were prepared by Siltech LLC, of Dacula, Ga. They are made by addition of ethylene oxide, propylene oxide or mixtures thereof to pentaerythritol (y=4), trimethyol propane (y=3). They conform to the following structure;

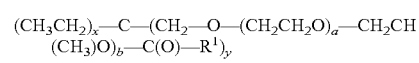

wherein;

a is an integer ranging from 0 to 4;

b is an integer ranging from 0 to 4, with the proviso that a+b ranges from 1 to 5;

$R^1$ is alkyl having 7 to 21 carbon atoms;

y is 4 or 3;

x equals 4−y.

Example 7-12

Pentaerytrhritol Examples (y=4 and x=0)

| Example | a | b |
|---------|---|---|
| 7 | 0 | 1 |
| 8 | 1 | 1 |
| 9 | 2 | 2 |
| 10 | 1 | 0 |
| 11 | 3 | 1 |
| 12 | 1 | 3 |

Example 13-20

Trimethyol Propane Examples (y=e and x=1)

| Example | a | b |
|---------|---|---|
| 13 | 0 | 1 |
| 14 | 1 | 1 |
| 15 | 2 | 2 |
| 16 | 1 | 0 |
| 17 | 3 | 1 |
| 18 | 1 | 3 |

Sorbitol Alkoxylates

Sorbitol is hexane-1,2,3,4,5,6-hexaol. It as a CAS number of 50-70-4

Sorbitol alkoxylates were prepared by Siltech LLC, of Dacula, Ga. They are made by addition of ethylene oxide, propylene oxide or mixtures thereof to sorbitol. They conform to the following structure;

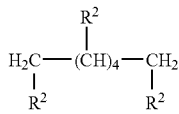

wherein;

$R^2$ is $-(CH_2CH_2O)_a-CH_2CH(CH_3)O)_b-H$ a is an integer ranging from 0 to 4;

b is an integer ranging from 0 to 4, with the proviso that a+b ranges from 1 to 5;

Examples 19-24

| Example | a | b |
|---|---|---|
| 19 | 0 | 1 |
| 20 | 1 | 1 |
| 21 | 2 | 2 |
| 22 | 1 | 0 |
| 23 | 3 | 1 |
| 24 | 1 | 3 |

Fatty Acids

Fatty Acids useful in the practice of the present invention are items of commerce they are available as either single components or mixtures.

Fatty Aid Names

Fatty Acids

Fatty acids useful as raw materials in the preparation of the compounds of the present invention are commercially available from a variety of sources including Procter and Gamble of Cincinnati Ohio. The structures are well known to those skilled in the art.

Saturated

| Example | R Formula | Common Name | Molecular Weight |
|---|---|---|---|
| 25 | $C_7H_5$ | caprylic | 144 |
| 26 | $C_9H_{19}$ | capric | 172 |
| 27 | $C_{11}H_{23}$ | lauric | 200 |
| 28 | $C_{13}H_{27}$ | myristic | 228 |
| 29 | $C_{14}H_{29}$ | pentadecanoic | 242 |
| 30 | $C_{15}H_{31}$ | palmitic | 256 |
| 31 | $C_{17}H_{35}$ | stearic | 284 |
| 32 | $C_{19}H_{39}$ | arachidinic | 312 |
| 33 | $C_{21}H_{43}$ | behenic | 340 |
| 34 | $C_{26}H_{53}$ | cetrotic | 396 |
| 35 | $C_{33}H_{67}$ | geddic acid | 508 |

Unsaturated

| Example | R Formula | Common Name | Molecular Weight |
|---|---|---|---|
| 36 | $C_{17}H_{33}$ | oleic | 282 |
| 37 | $C_{17}H_{31}$ | linoleic | 280 |
| 38 | $C_{17}H_{29}$ | linolenic | 278 |
| 39 | $C_{15}H_{29}$ | palmitoleic | 254 |
| 40 | $C_{13}H_{25}$ | myristicoleic | 226 |
| 41 | $C_{21}H_{41}$ | erucic | 338 |

Esterification Reactions

In addition to the ratio of polyoxyalkylene groups to fatty group and the linkage group chosen, it is very important for the practice of the current invention resulting in compounds of the present, the reaction of all of the hydroxyl groups to make esters is very important. The presence of unreacted hydroxyl groups in the compounds of the present invention is undesirable. The compounds of the present invention have very low amount of unreacted hydroxyl groups.

General Procedure

To the specified number of grams of the specified alkoxylate (Examples 1-24) is added the specified number of grams of the specified fatty acid (Example 25-41). Next add 0.1% by weight, based upon the total number of grams added of both alkoxylate and fatty acid. The reaction mass is heated to 190-200° C. Water is generated as the reaction proceeds. The reaction is followed as the acid value becomes vanishingly low. As the reaction proceeds vacuum is applied slowly to keep the water distilling off.

Examples 25-48

| | Alkoxylate | | Fatty Acid | |
|---|---|---|---|---|
| Example | Example | Grams | Example | Grams |
| 42 | 1 | 89.0 | 25 | 144.0 |
| 43 | 2 | 133.0 | 26 | 172.0 |
| 44 | 3 | 236.0 | 27 | 200.0 |
| 45 | 4 | 74.0 | 28 | 228.0 |
| 46 | 5 | 221.0 | 29 | 242.0 |

| | Alkoxylate | | Fatty Acid | |
|---|---|---|---|---|
| Example | Example | Grams | Name | Grams |
| 47 | 6 | 251.0 | 30 | 256.0 |
| 48 | 7 | 87.0 | 31 | 284.0 |
| 49 | 8 | 146.0 | 32 | 312.0 |
| 50 | 9 | 249.0 | 33 | 340.0 |
| 51 | 10 | 87.0 | 34 | 396.0 |
| 52 | 11 | 191.0 | 35 | 508.0 |
| 53 | 12 | 221.0 | 36 | 282.0 |
| 54 | 13 | 102.0 | 37 | 280.0 |
| 55 | 14 | 161.0 | 38 | 278.0 |
| 56 | 15 | 254.0 | 39 | 254.0 |
| 57 | 16 | 92.0 | 40 | 226.0 |
| 58 | 17 | 239.0 | 41 | 338.0 |
| 59 | 18 | 269.0 | 25 | 144.0 |
| 60 | 19 | 89.0 | 26 | 172.0 |
| 61 | 20 | 133.0 | 27 | 200.0 |
| 62 | 21 | 236.0 | 28 | 228.0 |
| 63 | 22 | 74.0 | 29 | 242.0 |
| 64 | 23 | 221.0 | 30 | 256.0 |
| 65 | 24 | 251.0 | 31 | 284.0 |

The reactions are held at temperature until the acid value and hydroxyl become vanishingly small and the saponification reacted almost theoretical. Products are used without additional purification. They are light in color and low in odor.

Applications Examples

Typical of the properties of the spider esters of the present invention are examples 44 and 53. Example 44 contains 45% by weight polyoxyalkylene group, having an HLB of 9. By HLB, this product should be milky in water forming a stable dispersion quite to the contrary it is a water insoluble oil. It is low in odor and has a very appealing feel on the skin. This ester solubilizers sunscreens to a much greater extent than mineral oil. The product of example 44 can be emulsified as an oil using a HLB of 5.6 emulsifier to make a cosmetically acceptable water resistant sun screen. Example 44 provides outstanding moisturization to the skin when evaluated by consumer panel.

Example 53 is 44% polyoxyalkylene containing. It has an HLB of 8.8. By HLB, this product should be milky in water forming a stable dispersion quite to the contrary it is a water insoluble oil. It is low in odor and has a very appealing feel on the skin. This ester solubilizers sunscreens to a much greater extent than mineral oil. The product of example 53 can be used to solubilize a variety of antioxidants and deliver them in an oil to the skin, providing protection from UV degradation. Example 53 provides outstanding moisturization to the skin when evaluated by consumer panel.

| Properties | | |
|---|---|---|
| | Example 44 | Example 53 |
| Appearance | Lt. Yellow Liquid | Yellow Liquid |
| Viscosity @25° C. | 120 cps | 260 cps |
| Water Solubility | Insoluble | Insoluble |
| Calculated HLB | 9.0 | 8.8 |
| Sun Screen Solubility | | |
| % weight  Sunscreen | Initial Appearance | Age Appearance[1] |
| 1%  Benzophenone 3 | Clear | Very Slight Haze[2] |
| 3%  Benzophenone 3 | Clear | Very Slight Haze[2] |
| 1%  Octylmethoxyciminate | Clear | Clear |

[1]Appearance after 48 hours at room temperature, 24 hours in refrigerator (37° F.) and 48 hours at room temperature.
[2]Slight haze was there since initial dissolution and did not increase with time.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claim be construed as encompassing all the features of patentable novelty which reside in the present invention, including all features which would be treated as equivalents thereof by those skilled in the art to which the invention pertains.

What is claimed:

1. A process for moisturizing the skin which comprises contacting the skin with an effective moisturizing concentration of a glycol spider esters conform to the following structure;

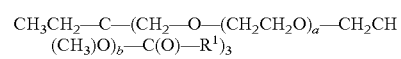

wherein;

a is an integer ranging from 0 to 4;

b is an integer ranging from 0 to 4, with the proviso that a+b ranges from 1 to 5;

$R^1$ is alkyl having 7 to 21 carbon atoms.

2. The process of claim 1 wherein a is 0.

3. The process of claim 1 wherein a is not 0 and b is not 0.

4. The process of claim 1 wherein a is 1, b is 1.

5. The process of claim 1 wherein $R^1$ is alkyl having 7 carbon atoms.

6. The process of claim 1 wherein $R^1$ is alkyl having 9 carbon atoms.

7. The process of claim 1 wherein $R^1$ is alkyl having 11 carbon atoms.

8. The process of claim 1 wherein $R^1$ is alkyl having 13 carbon atoms.

9. The process of claim 1 wherein $R^1$ is alkyl having 19 carbon atoms.

10. The process of claim 1 wherein $R^1$ is alkyl having 21 carbon atoms.

* * * * *